(12) United States Patent
Berndt

(10) Patent No.: US 6,633,369 B2
(45) Date of Patent: Oct. 14, 2003

(54) METHOD FOR MEASURING THE VOLUME OF INDIVIDUAL RED BLOOD CELLS

(75) Inventor: Klaus W. Berndt, Timonium, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 6 days.

(21) Appl. No.: 09/753,403

(22) Filed: Jan. 3, 2001

(65) Prior Publication Data

US 2002/0118354 A1 Aug. 29, 2002

(51) Int. Cl.[7] .................. G01N 33/48; G01N 15/02; G01N 21/03; G01N 21/59; G01B 11/22
(52) U.S. Cl. ................. 356/39; 356/627; 356/335; 436/165; 422/82.09
(58) Field of Search ................ 356/39, 317, 436, 356/440, 627, 335; 436/164, 165, 82.08; 422/87.05, 87.09

(56) References Cited

U.S. PATENT DOCUMENTS

| 5,427,959 | A | * | 6/1995 | Nishimura et al. | ......... 356/244 |
| 5,563,070 | A | * | 10/1996 | Yamamoto et al. | ............ 435/2 |
| 5,948,686 | A | * | 9/1999 | Wardlaw | ........................ 435/2 |
| 6,127,184 | A | * | 10/2000 | Wardlaw | .................... 356/244 |
| 6,235,536 | B1 | * | 5/2001 | Wardlaw | .................... 356/244 |

* cited by examiner

Primary Examiner—Zandra V. Smith
Assistant Examiner—Gordon J Stock
(74) Attorney, Agent, or Firm—Bruce S. Weintraub

(57) ABSTRACT

The invention discloses a method for determining the volume of individual red blood cells or other particles that are suspended in liquids. The sample is disposed into an optical cuvette suitable for microscopic analysis. An absorbing dye is added that does not leak into the cells, and that is able to absorb light at wavelengths that are only weakly absorbed by the cells. The cell volume is determined using transmitted light intensity values measured (i) in a first area comprising a single cell, (ii) in a second area close to that cell, and (iii) in said second area, after changing the cuvette thickness by a known amount.

52 Claims, 6 Drawing Sheets

METHOD FOR MEASURING THE VOLUME OF INDIVIDUAL RED BLOOD CELLS

FIELD OF THE INVENTION

The present invention relates to the field of quantitative microspectroscopy, and in particular to a method for measuring the volume of individual red blood cells.

BACKGROUND OF THE INVENTION

Determining the volume of individual red blood cells and, based on this measurement, calculating the Mean Cell Volume ("MCV") and the Red Cell Distribution Width ("RDW") is of clinical interest. Usually, systems based on electrical impedance measurement (Coulter Counter) or based on light scattering (Flow Cytometer) are employed (see. e.g., J. B. Henry, "Clinical diagnosis and management by laboratory methods", W. B. Saunders Company, Philadelphia, 1996, pp. 548 ff. or D. H. Tycko, M. H. Metz, E. A. Epstein, A. Grinbaum, "Flow-cytometric light scattering measurement of red blood cell volume and hemoglobin concentration", Applied Optics 24 (1985), 1355–1365). Impedance counters are complex and expensive instruments that require very careful adjustment and control of instrument and sample parameters. A major disadvantage of flow cytometers is the fact that the parameters of light scattering depend not only on cell volume, but also on the cell's shape.

In 1983, Gray, Hoffman and Hansen proposed a new optical method for determining the volume of cells in a flow cytometer (M. L. Gray, R. A. Hoffman, W. P. Hansen, "A new method for cell volume measurement based on volume exclusion of a fluorescent dye", Cytometry 3 (1983), 428–432). In this method, the cells are suspended in a fluorescent dye, which is unable to penetrate the cell membrane. The level of fluorescence, which is produced when a narrow stream of the cell suspension is excited by a focused laser beam, will remain constant until a cell arrives in the illuminated region thereby causing a decrease in fluorescence intensity, which is directly proportional to the volume of the cell. In a flow cytometer, a single cell is passing through the laser-illuminated spot within approximately 10. Due to this short data acquisition time interval, the electronic detection bandwidth has to be relatively large, which results in a poor signal-to-noise ratio and in a low precision for the volume determination.

The available data acquisition time can be significantly increased by suspending the cells in a stationary sample and applying digital imaging fluorescence microscopy (see P. L. Becker, F. S. Fay, "Cell-volume measurement using the digital imaging fluorescence microscope", Biophysical Journal 49 (1986), A465). In the digital fluorescence microscopy approach, a calibration procedure is required in order to determine the cell volume. Recktenwald and co-workers have introduced a method where the calibration is performed by means of optical transparent and non-fluorescent microspheres that are suspended together with the cells (D. Recktenwald, J. Phi-Wilson, B. Verwer, "Fluorescence quantitation using digital microscopy", Journal Physical Chemistry 97 (1993), 2868–2870). The volume of individual spheres is determined by measuring their projection area under the microscope and transforming this number into a volume, assuming an ideal spherical shape. The decrease in fluorescence intensity as a result of the spheres' volume that is being excluded from emitting fluorescence is used as the required calibration parameter. The advantage of this approach is given by the fact that the calibrating particles are located within the sample itself. In other words, a calibration is performed on the very same sample container, and no extra calibration sample is required.

The use of calibration spheres within a cell suspension is not without problems. First, the introduction of the spheres represents an additional step in the workflow. In systems that are designed for high throughput, this additional step would represent a disadvantage. Secondly, Recktenwald and co-workers observed a tendency of the fluorescent dye molecules to settle down on the sphere's surface, which causes an error. Third, if the optical index of refraction of the spheres does not match well with the liquid's index, then refraction-based artifacts in the measured fluorescence intensity occur at the edges of the spheres. And, finally, the use of microspheres can represent a problem, if, for example, a thin sample thickness in the order of a few micrometers or less is needed.

In view of the disadvantages and problems in the prior art as described above, there exists a need for a simple and reliable method for measuring the volume of individual red blood cells suspended in a liquid.

SUMMARY OF THE INVENTION

It is an objective of the present invention to provide a method for measuring the volume of individual red blood cells or other particles that are suspended in liquids.

According to the present invention, and for the case of red blood cells, the above objective is achieved by depositing a liquid sample that contains suspended red blood cells into an optical cuvette having an input window and an output window, by adding and evenly distributing an absorbing dye into the liquid that does not leak into the red blood cells, and that is able to absorb light at wavelengths that are only weakly absorbed by the red blood cells, by illuminating the sample through the input window at a wavelength that is absorbed by said dye, but only weakly absorbed by the red blood cells, by measuring the transmitted light intensity reemerging through the output window in an area that contains no red blood cells, by changing the cuvette thickness in that area by a well-defined amount and measuring the reemerging light intensity in the same area again, by measuring the reemerging light intensity in an area where a red blood cell resides, by measuring the reemerging light intensity in an area close to that same red blood cell, and by calculating the volume of the red blood cell based on these light intensity values and the known change in cuvette thickness.

BRIEF DESCRIPTION OF THE DRAWINGS

In FIG. 5, we assume a cylindrical cell of height, $h_{RBC}$.

DETAILED DESCRIPTION OF THE INVENTION

According to the method of the present invention, a liquid sample that contains suspended red blood cells is deposited into an optical cuvette having an input window and an output window. Preferably, the cuvette is relatively thin and suitable to be positioned onto the sample stage of a transmission microscope. For example, the cuvette can be built by placing a flexible #1 coverslip of 24 mm×50 mm size onto spacers that are residing on a common microscope slide of 25 mm×75 mm size. The preferred height of the spacers is approximately 200 μm. By pressing onto the flexible coverslip, thickness values in the center region of the cuvette between less than 1 μm and 200 μm can be achieved. An optical cuvette is any container that is able to hold a liquid sample within its interior space and that has a transparent entrance window and a transparent exit window, usually on opposite sides, allowing for transmission measurement. It would also be within the spirit of the invention to use a container with one transparent window on one side and a mirror on the other side. In this case, light would enter the container through said one transparent window, would cross the liquid sample twice, and would exit the container through the same window. The one window would function as both entrance window and exit window. The invention is not limited to containers for microscopic analysis, but is applicable also for containers of larger size that are interrogated on optical systems other than microscopes.

An absorbing dye is added to, and evenly distributed within the liquid sample. The dye is selected so that it does not leak into the red blood cells. Also, it should absorb excitation light within a spectral region where the absorption within the red blood cells is only weak. Since hemoglobin is the dominant absorber in red blood cells, the illumination wavelength has to be longer than 600 nm. One good candidate dye is TO-PRO-3 (sold, for example, by Molecular Probes, Inc., Eugene, Oreg.), that can be illuminated within a wavelength range around to 640 nm, where it has an absorption coefficient of 1.14 * $10^5$ L/Mcm. Another possible dye would be TO-PRO-5 (sold by Molecular Probes, Inc.), which also does not penetrate into the red blood cells, can be illuminated around 750 nm, and has an absorption coefficient of 1.21 * $10^5$ L/Mcm.

It is apparent to one skilled in the art that the invention is not limited to the two dyes mentioned above. Many other dyes are available that fulfill the spectral conditions for measurements on red blood cells, and even more dyes are available that fulfill the spectral conditions for other particles. It would of course also still be within the spirit of the present invention to add and evenly distribute the absorbing dye within the liquid sample prior to disposing the sample into the container.

Figure 1:
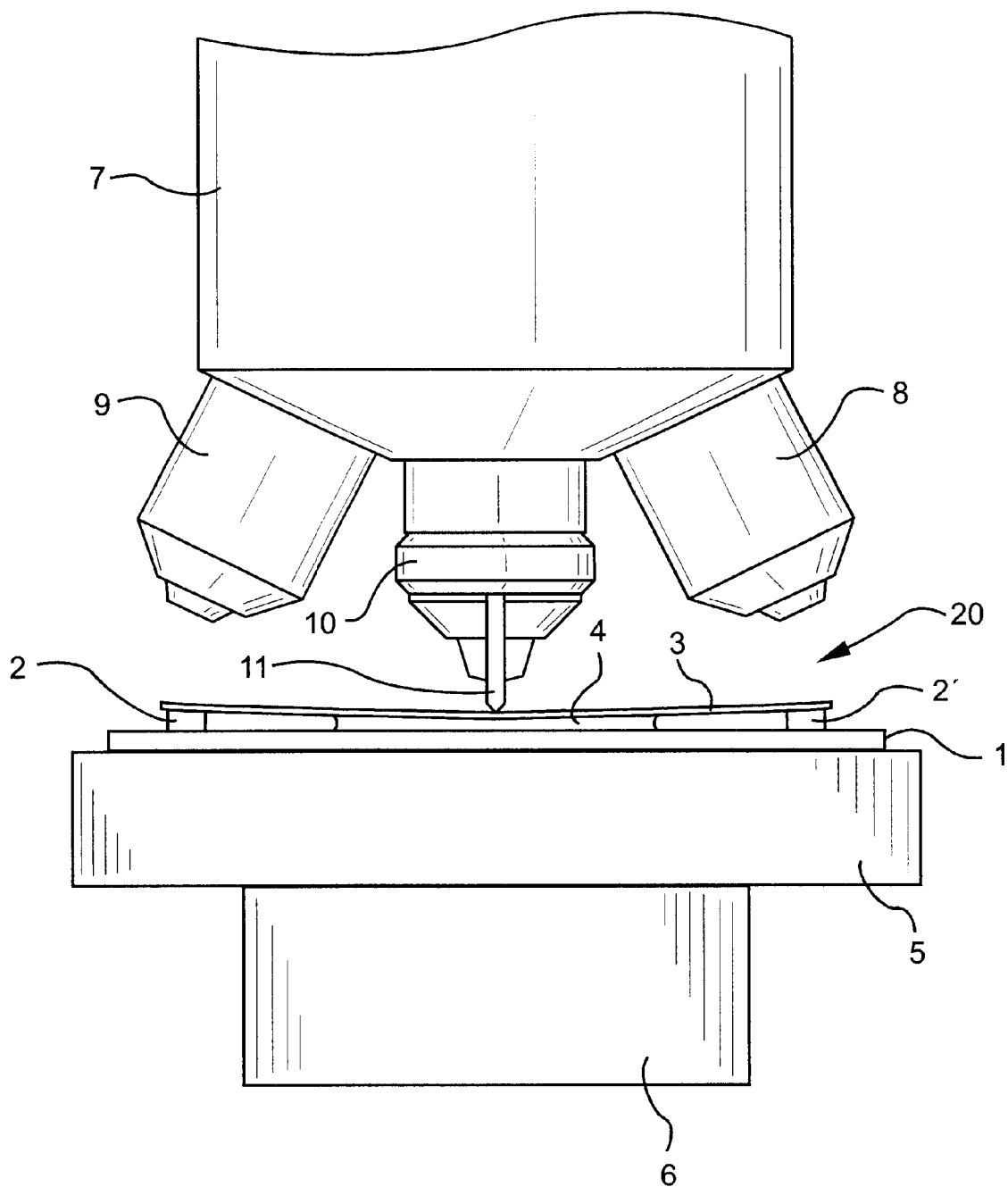
FIG. 1 depicts a measuring setup with an optical cuvette having a stiff input window and a flexible output window, and containing a liquid sample comprising suspended red blood cells.
Figure 2:
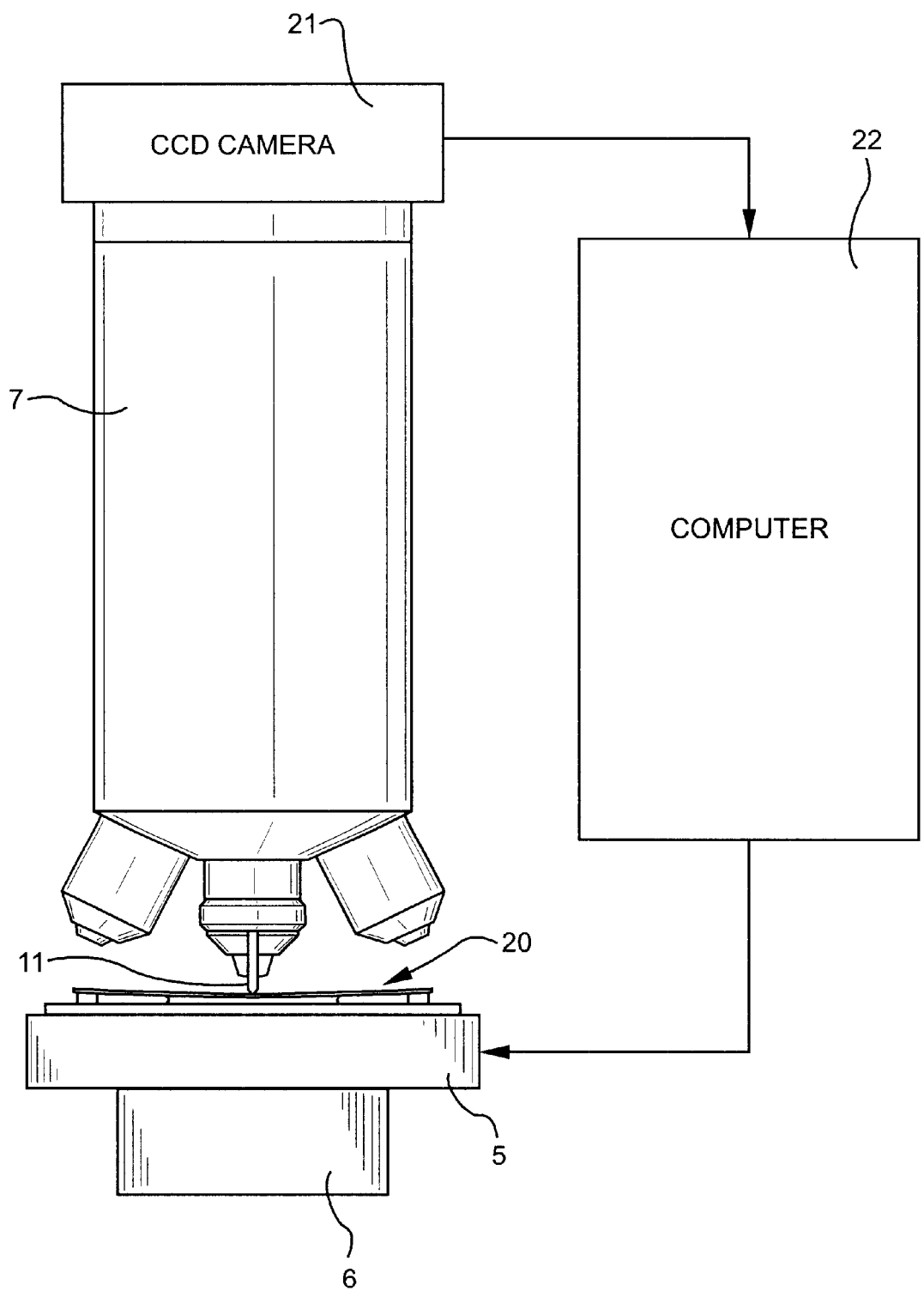
FIG. 2 illustrates a complete set-up comprising sample container, XYZ-stage, transmission microscope, CCD camera, and computer.

FIG. 1 depicts a measuring set-up with an optical cuvette (20) having a stiff input window (1), a flexible output window (3) and containing a liquid sample (4) comprising suspended red blood cells. The cuvette is built by using a common microscope slide (1) that carries spacers (2, 2') to hold a flexible cover slip (3). The suspension of red blood cells in a liquid such as blood plasma (4) is contained between slide (1) and cover slip (3) The optical cuvette is positioned on an XYZ-stage (5) of a common transmission microscope (7) having interchangeable objective lenses (8, 9, and 10) and a sample illumination source (6). As shown in FIG. 2, microscope (7) is equipped with a CCD camera (21) that is connected to a computer (22) for storing data and performing image-processing procedures. Computer (22) is also connected to XYZ-stage (5) to move cuvette (20) as needed.

Figure 3:
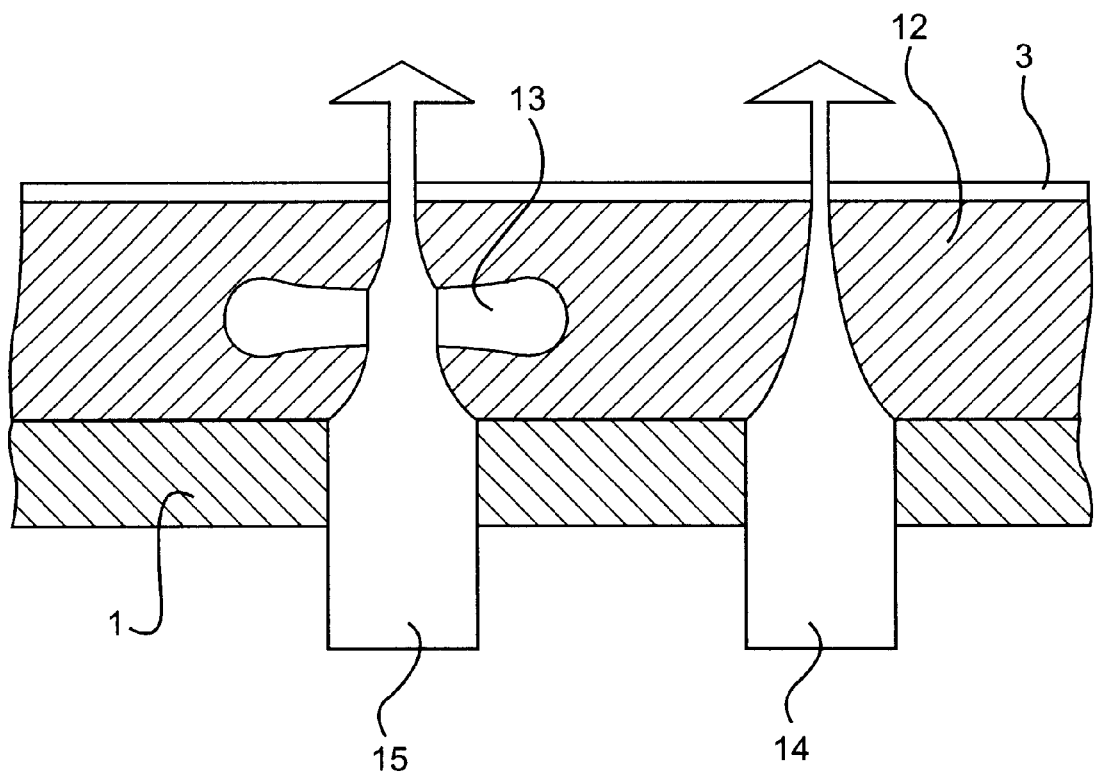
FIG. 3 shows schematically an optical cuvette with a region containing a weakly absorbing red blood cell, and another region containing no cells. The arrows illustrate the stream of photons traversing the sample, whereby the decrease in width is meant as an indication of the decreasing light intensity as a result of absorption.

FIG. 3 shows schematically an optical cuvette having a stiff input window (1) and a flexible output window (3), with a region containing a weakly absorbing red blood cell (13), and another region containing no cells. The arrows (14) and (15) illustrate the stream of photons traversing the sample, whereby the decrease in width is meant as an indication of the decreasing light intensity as a result of light absorption within liquid portion (12) of the sample. As indicated in FIG. 3, the optical absorption within red blood cell (13) is so weak that no decrease in intensity occurs. In operation, and referring again to FIGS. 1 and 2, cuvette (20) is moved upwards by means of stage (5) until flexible window (3) comes into physical contact with a fixed plunger (11) that is mounted onto objective lens (10) in such a way that the focal plane of microscope (7) lies within liquid sample (4) if flexible window (3) is touching plunger (11). If necessary, cuvette (20) is being moved in X- and Y-directions until a sample area containing no red blood cells comes into the field of view. If the sample is whole blood, then it is appropriate to use a cuvette thickness in the range of 2 μm to 30 μm in order to have areas containing no red blood cells readily available. For diluted blood samples, thicker cuvettes can be used.

Figure 4:
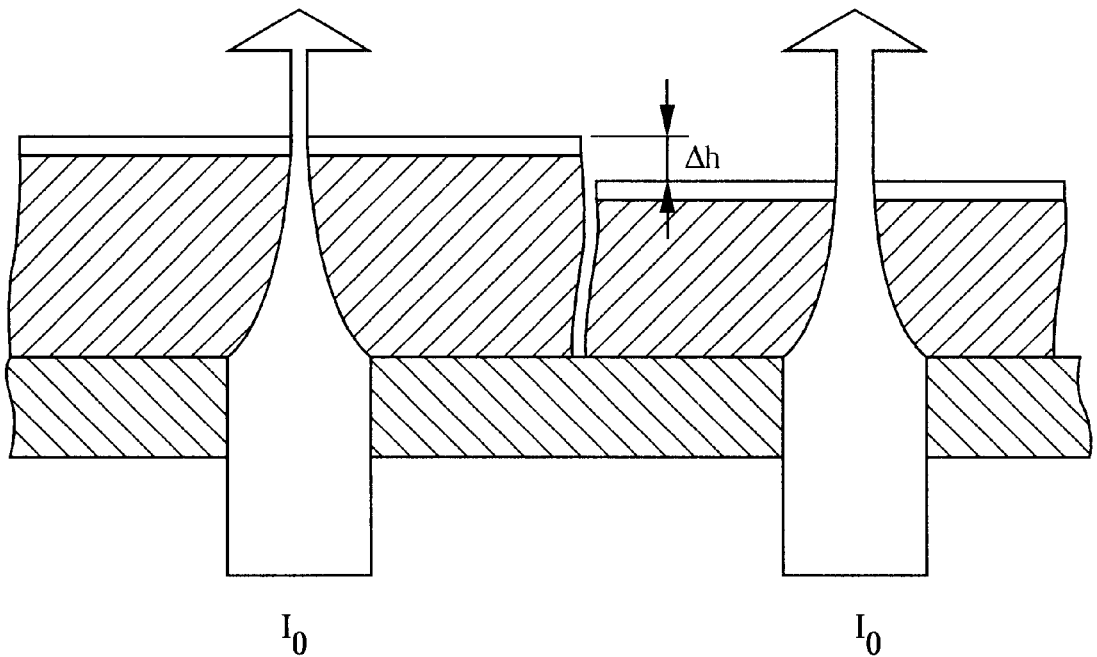
FIG. 4 illustrates the calibration procedure, where the cuvette thickness in an area that contains no red blood cells is changed by a well-defined amount, $\Delta h$, and the reemerging light intensities, $I_1$ and $I_2$, are measured prior to and after changing the thickness. In this example, the cuvette thickness has been reduced.

Once an area containing no red blood cells has been found, the sample is illuminated with light of appropriate wavelength by means of illumination source (6), and the reemerging intensity of the transmitted light, $I_1$, in that area is measured by means K of CCD camera (21), and the result stored in computer (22). This is illustrated in FIG. 4. In a next step, cuvette (20) is moved further upwards by means of stage (5) by a small, but precisely known distance, h. Moving cuvette (20) upward against fixed plunger (11) results in a reduction in the optical path length within the cuvette by an amount identical to h. When cuvette (20) has been moved, a new reemerging light intensity, $I_2$, in the same area is measured, and the result stored in computer (22). The new light intensity, $I_2$, has a higher value than the first intensity, $I_1$, because a smaller sample thickness results in less absorption of light within the sample.

The two reemerging light intensity values, $I_1$ and $I_2$, together with the change in optical path length, h, can be used to calibrate the set-up by calculating a ratio "change in reemerging light intensity/change in sample thickness". Referring to FIG. 4, this calibration can be explained as follows.

Assuming that the liquid sample is evenly illuminated by excitation light, the first reemerging light intensity, $I_1$, is given by $$I_1 = I_0 * 10^{-ac*h_1} \quad (1)$$

where $I_0$ is the illumination intensity, a is the absorption coefficient of the light-absorbing dye c is the concentration of the dye. The quantity $h_1$ is the optical path length (or thickness) of cuvette (20) at the area that is measured.

The light intensity, $I_2$, which is measured after changing the cuvette thickness by an amount of h is given by $$I_2 = I_0 * 10^{-ac*(h_1 - \Delta h)} \quad (2)$$

By dividing equation (2) by equation (1), and by taking the logarithm, we obtain an expression for the product a*c, which represents our calibration quantity:

$$a*c = \frac{lg\left(\frac{I_2}{I_1}\right)}{\Delta h}. \quad (3)$$

Equation (3) indicates that there is no need for knowing the absolute cuvette thickness, $h_1$, or for measuring the illumination intensity, $I_0$, because these two quantities are canceled out.

Figure 5:
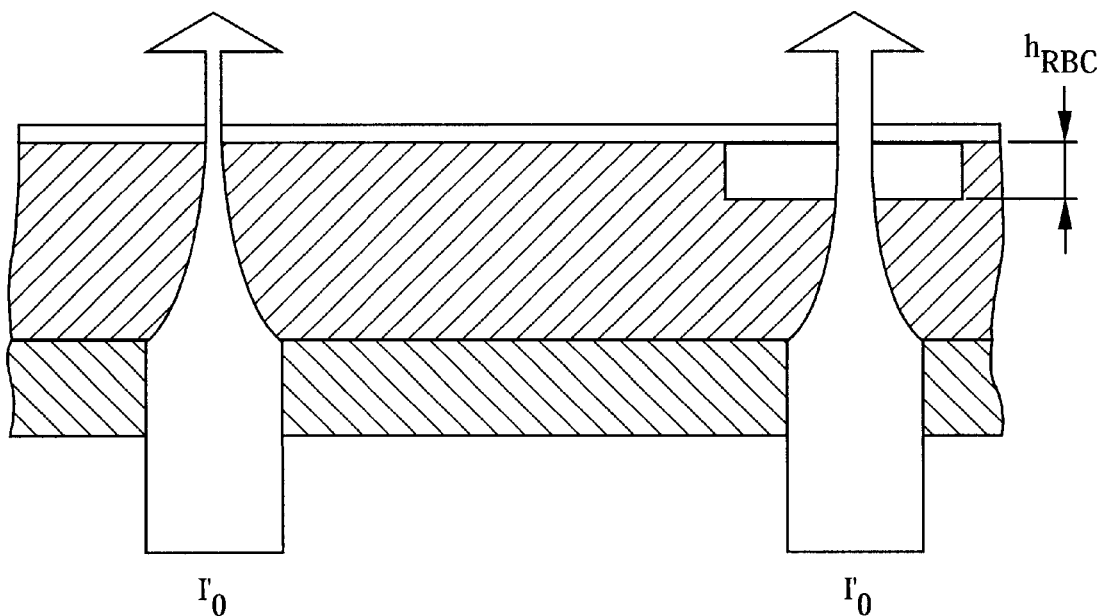
FIG. 5 illustrates the measuring procedure, where the reemerging light intensities, $I_4$ and $I_3$, are measured in an area where a red blood cell resides, and in an area close to that same cell.

After performing a calibration as outlined above, in the method according to the present invention, the volume of a single red blood cell is determined in the following way:

In a first step, the reemerging light intensity, $I_4$, is measured in an area, $A_{RBC}$, where a red blood cell resides. For the moment, we assume that the red blood cell has a cylindrical shape of area $A_{RBC}$, and of height $h_{RBC}$ (see FIG. 5). We also assume a height of the liquid sample layer, $h_2$, which has not to be equal to $h_1$, and an illumination intensity, $I'_0$, which has not to be identical to $I_0$. Under these conditions, we obtain $$I_4 = I'_0 * 10^{-ac*(h_2 - h_{RBC})} \quad (4)$$

for the reemerging light intensity.

In a second step, the reemerging light intensity, $I_3$, is measured in an area of identical size, $A_{RBC}$, close to that same red blood cell. Under the same conditions as for $I_4$, we obtain $$I_3 = I'_0 * 10^{-ac*h_2} \quad (5)$$

Dividing equation (4) by equation (5), we obtain $$lg\left(\frac{I_4}{I_3}\right) = ac * h_{RBC} \quad (6)$$

$$h_{RBC} = \frac{lg\left(\frac{I_4}{I_3}\right)}{a*c}. \quad (7)$$

For a cylindrical cell of area $A_{RBC}$, the cell volume, $V_{RBC}$, can be calculated by multiplying the cell area by the cell height as given in equation (7), which results in $$V_{RBC} = A_{RBC} * h_{RBC} = A_{RBC} * \frac{lg\left(\frac{I_4}{I_3}\right)}{a*c}, \quad (8)$$

or, with equation (3) for the product a*c, in $$V_{RBC} = A_{RBC} * \Delta h * \frac{lg\left(\frac{I_4}{I_3}\right)}{lg\left(\frac{I_2}{I_1}\right)}. \quad (9)$$

Equation (9) shows that the method according, to the present invention is base on differential measurements regarding the thickness of the cuvette, and on ratiometric measurements regarding the reemerging light intensities. In other words, there is no need to know the absolute thickness of the cuvette. Moreover, there is no need to know the excitation intensity which is injected into the cuvette.

Equation (9) shows also that any long-term drift in the instrumental parameters is canceled out. This results from the fact that the volume of a red blood cell, $V_{RBC}$, is calculated from a ratio of photocurrents. In other words, if the calibration procedure is executed closely in time with the measurement, then the method according to the present invention is very robust. This condition will always be fulfilled, since the calibration procedure is performed on the very same sample that is being measured.

So far, it has been assumed that the red blood cell has a cylindrical shape. It can be shown that the shape of the red blood cell can be irregular and that the Z-position of the cell within the cuvette has no impact on the calculated cell volume. The volume of a cell, $V_{RBC}$, is related to the spatially dependent cell height, $h_{REC}(,)$, via the equation $$V_{RBC} = \int h_{RBC}(\xi, \eta) d\xi d\eta \quad (10)$$

In equation (10), the quantities and represent the independent X- and Y-variables within the red blood cell. The required integration is easily performed by adding the pixel intensities, $I_1(,)$, within the area. $A_{RBC}$, that is being occupied by the red blood cell on the photosensitive $$V_{RBC} = (1/ac) * \int lg\left(\frac{I_4(\xi, \eta)}{I_3}\right) d\xi d\eta, \quad (11)$$

target of the CCD camera. Combining equations (7) and (10) results in which represents the final expression for the red blood cells volume as determined according to the present invention.

The integration procedure shown in equation (11) has not to be performed exactly over the area occupied by a red blood cell. Instead, it could be performed over a somewhat larger area that includes the cell. Outside of the cell, $I_4(\xi,\eta)$ is identical to $I_{13}$; therefore $lg[I_4(\xi,\eta)/I_3]=0$. In other words, extending the integration over a larger area beyond the cell's perimeter would not result in additional contributions to the calculated cell volume. This aspect of the invention allows for the use of simple one-size one-shape integration areas for all individual cells that are studied. Consequently, the required calculations can be executed within a shorter time interval. It should be noted that it is assumed, as equation (11) implies, that the intensity $I_3$ near the cell is constant. While $I_4(\xi,\eta)$ is measured in practice as an intensity of single CCD pixels, $I_3$ can be determined with maximum precision as the sum of all pixel intensities over an area, divided by the number of pixels. In other words, $I_3$ is the average pixel intensity near the cell.

Figure 6:
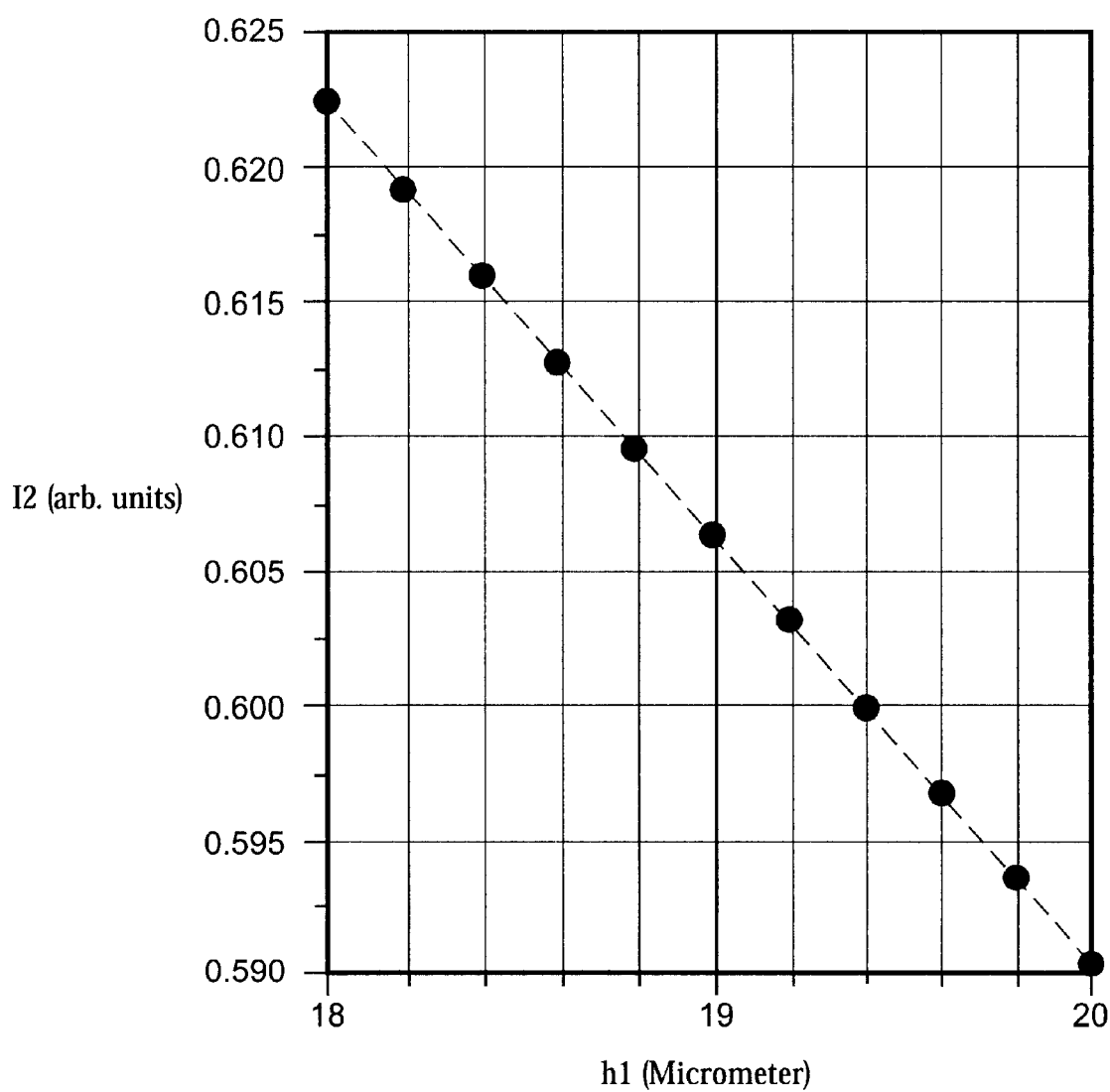
FIG. 6 shows a calculated plot of reemerging light intensity in arbitrary units, if a cuvette thickness of approximately 18 μm is increased in ten steps of 0.2 μm each, up to approximately 20 μm. In this example, TO-PRO-3 in a concentration c=1 mM/L has been assumed as the absorbing dye, which has an absorption coefficient a=1.144 * $10^5$ L/M cm at 640 nm wavelength.

In order to enhance the calibration precision, it is possible to employ more than one change, h, in cuvette thickness. FIG. 6 shows a calculated plot of reemerging light intensity in arbitrary units, if a cuvette thickness of approximately 18 $\mu$m is increased in ten steps of 0.2 $\mu$m each, up to approximately 20 $\mu$m. In this example, TO-PRO-3 in a concentration c=1 mM/L has been assumed as the absorbing dye, which has an absorption coefficient a=1.144 * $10^5$. L/M cm at 640 nm wavelength. As can be seen from FIG. 6, within the relatively small range of change in thickness, the light intensity as a function of thickness can be represented by a straight-line relationship. Using the full 5.4-% change in intensity shown by the dashed line in FIG. 6, which represents the best fit, we calculate a value of a*c=lg(0.6223/ 0.5903)/(2.0* $10^{-4}$ cm)=114.63 $cm^{-1}$, which, of course, matches well with the expected value of 114.44 $cm^{-1}$.

The method for measuring the volume of individual red blood cells according to the present invention can be applied to whole blood or to diluted blood samples. The present invention can also be applied to a whole cluster of red blood cells or other particles in a liquid suspension, and not only to individual particles or cells. It would also be within the spirit of the invention to apply this method to other particles suspended in liquids such as beads or other particles or cells, for example, prokaryotic, bacterial, eukaryotic, mammalian, tissue culture or human cells. It is also apparent to one skilled in the art that the present invention can also be applied to particles or cells in other liquid suspensions or samples or dilutions thereof, such other medical or biological samples including tissue cultures or other cells in culture, including bacterial cultures, and other body fluids such as blood, urine, sputum, saliva and lymph fluid.

Depending on the optical properties of a liquid sample, the method can also be applied in cuvettes of higher thickness. Using a flexible window is only one example for achieving a change in the thickness of the cuvette. It would also be possible to use a stiff window, but spacers made out of a flexible material such as rubber. Still another embodiment would be possible by utilizing a flexible cuvette wall instead of localized spacers. Also, the change in cuvette thickness can be achieved by leaving the main part of the cuvette fixed, and acting with a positive or negative force onto the window, so that the window is moving. Such positive or negative forces may even involve the use of pressure or vacuum.

As has been already mentioned above, the invention is not limited to optical microscopes. Any imaging system that allows measuring transmitted light intensities in areas that contain a particle and in areas that do not contain a particle are suitable to practice the present invention. The imaging system may contain lenses, but may also use fiber-optic elements in so-called proximity configurations. In this case, a coherent fiber-optic bundle is arranged between a cuvette window and an imaging photodetector. Finally, it would still be within the spirit of the present invention to scan a beam of light across the cuvette windows and to monitor the transmitted light with a non-imaging photodetector, while the thickness of the cuvette is changing.

It should be mentioned that the step of calibration, i.e. determining the quantity "change in reemerging light intensity/change in sample thickness" according to equation (3) can also be performed in close proximity to the particle under investigation. In this case, and referring to FIG. 4, one would measure first the reemerging light intensity in the neighborhood of a single particle. In a next step, the thickness of the optical cuvette in this area is being changed by an amount $\Delta h$, and new reemerging light intensity is measured. In a third step, the reemerging light intensity in the area occupied by the particle is measured. While the first two steps provide the required calibration, the second and the third step provide the two reemerging light intensity values that are needed for the actual volume measurement. This second procedure according to the present invention has the advantage that three instead of four steps are required. The first procedure according to the present invention allows performing the calibration within a cuvette area of increased thickness, which would allow for a more precise calibration value due to the increased reemerging light intensity levels. In practice, the user has to decide, based on the priorities at hand.

While the present invention is described herein in terms of certain preferred embodiments, those skilled in the art will recognize that various modifications and improvements may be made to the invention without departing from the scope thereof. Moreover, although individual features of one embodiment are not in other embodiments, it would be apparent that individual features of one embodiment may be combined with one or more features of another embodiment or features from a plurality of embodiments.

What is claimed is:

1. A method for measuring the volume of particles in a liquid, the method comprising:
   (a) obtaining a suspension of particles in a liquid;
   (b) depositing said suspension into a container, said container being suitable to perform transmission measurements;
   adding an absorbing dye to said suspension in said container that does not substantially leak into said particles, wherein said dye is able to absorb excitation light at wavelengths that are only weakly absorbed by said particles;
   (c) illuminating said suspension with light, whereby the wavelength of said light is selected so that said light is being absorbed by said dye, but only weakly absorbed by said particles;
   (d) measuring a first intensity of transmitted light that reemerges from said suspension in a first area of said suspension, wherein said first area contains no particles;
   (e) changing the thickness of said container in said first area by a known amount by pressing on said container from outside of said container and measuring a second intensity of transmitted light that reemerges from said suspension in said first area;
   (f) measuring a third intensity of transmitted light that reemerges from said suspension in a second area of said suspension wherein said second area contains at least one particle;
   (g) measuring a fourth intensity of transmitted light that reemerges from a third area of said suspension close to said at least one particle in said second area; and
   (h) determining the volume of said at least one particle based on said transmitted light intensity values and said known change in thickness of said container.

2. A method for measuring the volume of particles in a liquid, the method comprising:
   (a) obtaining a suspension of particles in a liquid;
   (b) adding an absorbing dye to said suspension forming a mixture, wherein said dye does not substantially leak into said particles and is able to absorb excitation light at wavelengths that are only weakly absorbed by said particles;

(c) depositing said mixture into a container, said container being suitable to perform transmission measurements;

(d) illuminating said mixture with light, whereby the wavelength of said light is selected so that said light is being absorbed by said dye but only weakly absorbed by said particles;

(e) measuring a first intensity of transmitted light that reemerges from said mixture in a first area of said mixture, wherein said first area contains no particles;

(f) changing the thickness of said container in said first area by a known amount by pressing on said container from outside of said container and measuring a second intensity of transmitted light that reemerges from said mixture in said first area;

(g) measuring a third intensity of transmitted light that reemerges from said mixture in a second area of said mixture wherein said second area contains at least one particle;

(h) measuring a fourth intensity of transmitted light that reemerges from a third area of said mixture close to said at least one particle in said second area; and (i) determining the volume of said at least one particle based on said transmitted light intensity values and said known change in thickness of said container.

3. The method of claim 1 wherein the particle is a cell.

4. The method of claim 2 wherein the particle is a cell.

5. The method of claim 3 wherein the cell is a human cell.

6. The method of claim 4 wherein the cell is a human cell.

7. The method of claim 3 wherein the cell is a red blood cell.

8. The method of claim 4 wherein the cell is a red blood cell.

9. The method of claim 1 wherein the liquid is a biological or medical sample.

10. The method of claim 2 wherein the liquid is a biological or medical sample.

11. The method of claim 9 wherein the biological or medical sample comprises a body fluid.

12. The method of claim 10 wherein the biological or medical sample comprises a body fluid.

13. The method of claim 11 wherein the body fluid is selected from the group consisting of blood, urine, sputum, saliva and lymph fluid.

14. The method of claim 12 wherein the body fluid is selected from the group consisting of blood, urine, sputum, saliva and lymph fluid.

15. The method of claim 9 wherein the biological or medical sample comprises tissue culture cells.

16. The method of claim 10 wherein the biological or medical sample comprises tissue culture cells.

17. The method of claim 9 wherein the biological or medical sample comprises bacterial cells.

18. The method of claim 10 wherein the biological or medical sample comprises bacterial cells.

19. The method of claim 2 wherein the container is an optical cuvette.

20. The method of claim 1 wherein the container is an optical cuvette.

21. The method of claim 19 wherein the optical cuvette comprises an input window and an output window.

22. The method of claim 20 wherein the optical cuvette comprises an input window and an output window.

23. The method of claim 19 wherein the optical cuvette comprises a microscope slide and a cover slip.

24. The method of claim 20 wherein the optical cuvette comprises a microscope slide and a cover slip.

25. The method of claim 1 wherein the dye is selected from the group consisting of TO-PRO-3 and TO-PRO-5.

26. The method of claim 2 wherein the dye is selected from the group consisting of TO-PRO-3 and TO-PRO-5.

27. A method for measuring the volume of particles in a liquid, the method comprising:

(a) obtaining a suspension of particles in a liquid;

(b) depositing said suspension into a container, said container being suitable to perform transmission measurements;

(c) adding an absorbing dye to said suspension in said container that does not substantially leak into said particles and that is able to absorb excitation light at wavelengths that are only weakly absorbed by said particles;

(d) illuminating said suspension with light, whereby the wavelength of said light is selected so that the light is being absorbed by said dye but only weakly absorbed by said particles;

(e) measuring a first intensity of transmitted light that reemerges from said suspension in a first area of said suspension, wherein said first area is located close to a particle;

(f) changing the thickness of said container in said first area by a known amount by pressing on said container from outside of said container and measuring a second intensity of transmitted light that reemerges from said suspension in said first area;

(g) measuring a third intensity of transmitted light that reemerges from said suspension in a second area of said suspension, wherein said second area contains at least one particle; and (h) determining the volume of said at least one particle based on said transmitted light intensity values and said known change in thickness of said container.

28. A method for measuring the volume of particles in a liquid, the method comprising:

(a) obtaining a suspension of particles in a liquid;

(b) adding an absorbing dye to said suspension forming a mixture, wherein said dye does not substantially leak into said particles and is able to absorb excitation light at wavelengths that are only weakly absorbed by said particles;

(c) depositing said mixture into a container, said container being suitable to perform transmission measurements;

(d) illuminating said mixture with light, whereby the wavelength of said light is selected so that the light is being absorbed by said dye but only weakly absorbed by said particles;

(e) measuring a first intensity of transmitted light that reemerges from said mixture in a first area of said mixture, wherein said first area is located close to a particle;

(f) changing the thickness of said container in said first area by a known amount by pressing on said container from outside of said container and measuring a second intensity of transmitted light that reemerges from said mixture in said first area;

(g) measuring a third intensity of transmitted light that reemerges from said mixture in a second area of said mixture, wherein said second area contains at least one particle; and (h) determining the volume of said at least one particle based on said transmitted light intensity values and said known change in thickness of said container.

29. The method of claim 27 wherein the particle is a cell.

30. The method of claim 28 wherein the particle is a cell.

31. The method of claim 29 wherein the cell is a human cell.

32. The method of claim 30 wherein the cell is a human cell.

33. The method of claim 29 wherein the cell is a red blood cell.

34. The method of claim 30 wherein the cell is a red blood cell.

35. The method of claim 27 wherein the liquid is a biological or medical sample.

36. The method of claim 28 wherein the liquid is a biological or medical sample.

37. The method of claim 35 wherein the biological or medical sample comprises a body fluid.

38. The method of claim 36 wherein the biological or medical sample comprises a body fluid.

39. The method of claim 37 wherein the body fluid is selected from the group consisting of blood, urine, sputum, saliva and lymph fluid.

40. The method of claim 38 wherein the body fluid is selected from the group consisting of blood, urine, sputum, saliva and lymph fluid.

41. The method of claim 35 wherein the biological or medical sample comprises tissue culture cells.

42. The method of claim 36 wherein the biological or medical sample comprises tissue culture cells.

43. The method of claim 35 wherein the biological or medical sample comprises bacterial cells.

44. The method of claim 36 wherein the biological or medical sample comprises bacterial cells.

45. The method of claim 27 wherein the container is an optical cuvette.

46. The method of claim 28 wherein the container is an optical cuvette.

47. The method of claim 45 wherein the optical cuvette comprises an input window and an output window.

48. The method of claim 46 wherein the optical cuvette comprises an input window and an output window.

49. The method of claim 45 wherein the optical cuvette comprises a microscope slide and a cover slip.

50. The method of claim 46 wherein the optical cuvette comprises a microscope slide and a cover slip.

51. The method of claim 27 wherein the dye is selected from the group consisting of TO-PRO-3 and TO-PRO-5.

52. The method of claim 28 wherein the dye is selected from the group consisting of TO-PRO-3 and TO-PRO-5.

\* \* \* \* \*